United States Patent
Lee et al.

(10) Patent No.: US 6,793,657 B2
(45) Date of Patent: Sep. 21, 2004

(54) SPINE FIXING APPARATUS

(75) Inventors: Choon Ki Lee, 6-506 Jinjoo Apt., 20-4, Shinchon-dong, Songpa-ku, Seoul, 138-240 (KR); Cheol Sang Kim, Chonju-shi (KR); Sung Pil Choi, Chonju-shi (KR); Duc Soo Moon, Seoul (KR); Sang Soo Park, Seoul (KR); Seayoung Ahn, Bethesda, MD (US)

(73) Assignees: Solco Biomedical Co., Ltd., Kyungki-Do (KR); Choon Ki Lee, Seoul (KR)

( * ) Notice: Subject to any disclaimer, the term of this patent is extended or adjusted under 35 U.S.C. 154(b) by 0 days.

(21) Appl. No.: 09/949,583

(22) Filed: Sep. 10, 2001

(65) Prior Publication Data

US 2003/0050640 A1 Mar. 13, 2003

(51) Int. Cl.$^7$ .............................................. A61B 17/70
(52) U.S. Cl. ....................................................... 606/61
(58) Field of Search .............................. 606/60, 61, 72, 606/73

(56) References Cited

U.S. PATENT DOCUMENTS

| | | | |
|---|---|---|---|
| 5,443,467 A | * 8/1995 | Biedermann et al. | ......... 606/65 |
| 5,474,555 A | * 12/1995 | Puno et al. | .................... 606/73 |
| 5,693,053 A | * 12/1997 | Estes | ........................... 606/61 |
| 5,989,251 A | * 11/1999 | Nichols | ........................ 606/61 |
| 6,217,578 B1 | * 4/2001 | Crozet et al. | .................. 606/61 |
| 6,264,658 B1 | * 7/2001 | Lee et al. | ...................... 606/61 |
| 6,273,889 B1 | 8/2001 | Richelsoph | |
| 6,432,108 B1 | * 8/2002 | Burgess et al. | ................ 606/61 |
| 6,565,565 B1 | * 5/2003 | Yuan et al. | .................... 606/61 |
| 2001/0007072 A1 | * 7/2001 | Steiner et al. | ................ 606/57 |
| 2001/0047171 A1 | * 11/2001 | Troxell et al. | ................ 606/61 |
| 2002/0143330 A1 | * 10/2002 | Shluzas | ....................... 606/61 |

* cited by examiner

Primary Examiner—Michael B. Priddy
(74) Attorney, Agent, or Firm—Birch, Stewart, Kolasch & Birch, LLP

(57) ABSTRACT

A spine-fixing apparatus includes a plurality of spine screw members fixed to a spine in a predetermined interval, a pair of rods coupled to the spine screw members for supporting the spine, a plurality of fixing nuts coupled to the spine screw members, and a plurality of pressing pieces interposed between the fixing nuts and the spine screw members for pressing and fixing the rods.

4 Claims, 6 Drawing Sheets

SPINE FIXING APPARATUS

BACKGROUND OF THE INVENTION

1. Field of the Invention

The present invention relates to a spine fixing apparatus capable of suitably fixing an unstable spine caused by a fracture or disease by adjusting angle and width between rods of the apparatus according to a curvature shape of the spine, and simplifying assembly process thereof so as to reduce overall assembly time.

2. Description of the Related Art

Generally, when a spine is fractured or diseased, the spine must be fixed. As such, a number of methods for fixing unstable spine have been developed. Among them is to place the spine as it were and fix it with a spine-fixing device. Typically, the spine-fixing device has two rods arranged along the spine so as to be fixed with screws thereon and connectors bridging the rods for fixing each other such that the spine is supported by the rods.

In the conventional spine fixing device, however, the screws are coupled to the spine integral with the rods and the two rods are fixedly coupled each other using the connectors such that the connector cannot be adjusted in a lateral and vertical directions thereby failing to fix the spine in the suitable position.

Furthermore, since the connector has a fixed length, the connector cannot bridge the two rods when the distance or angle between the rods are changed.

SUMMARY OF THE INVENTION

The present invention has been made in an effort to solve the above problems.

It is an object of the invention to provide a spine-fixing apparatus capable of reliably fixing the unstable spine, caused by a fracture or disease, by adjusting distance and angle between rods, which arranged along the spine, of the fixing-apparatus according to a shape of the spine.

It is another object of the present invention to provide a spine fixing-apparatus which enables each fixing nut to correctly fastened with the upper end of each spine screw member thereby preventing any erroneous coupling therebetween.

It is further another object of the present invention to provide a spine-fixing apparatus capable of simplifying installation process and reducing overall installation time as well as reliable installation by integrally forming a screw portion of a spine screw member, a supporting member for supporting a rod, and a cover for the supporting member of the spine-fixing apparatus.

To achieve the above objects, a spine-fixing apparatus of the present comprises a plurality of spine screw members fixed to a spine in a predetermined interval, a pair of rods coupled to the spine screw members for supporting the spine, a plurality of fixing nuts coupled to the spine screw members, and a plurality of pressing pieces interposed between the fixing nuts and the spine screw members for pressing and fixing the rods.

BRIEF DESCRIPTION OF THE DRAWINGS

The accompanying drawings, which are incorporated in and constitute a part of the specification, illustrate an embodiment of the invention, and together with the description, serve to explain the principles of the invention.

DETAILED DESCRIPTION OF THE PREFERRED EMBODIMENT

A preferred embodiment of the present invention will be described hereinafter with reference to the accompanying drawings.

Figure 1:
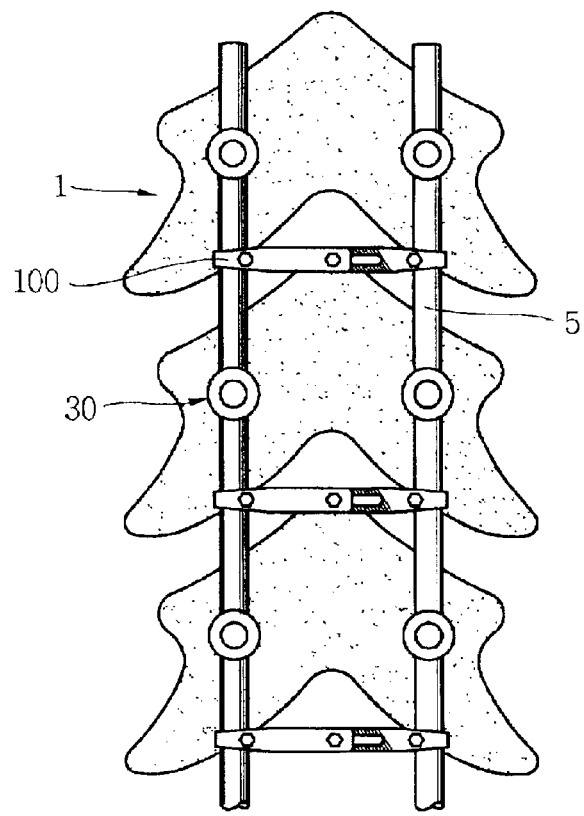
FIG. 1 is a front elevation view of a spine-fixing apparatus installed on a spine according to a first embodiment of the invention.
Figure 2:
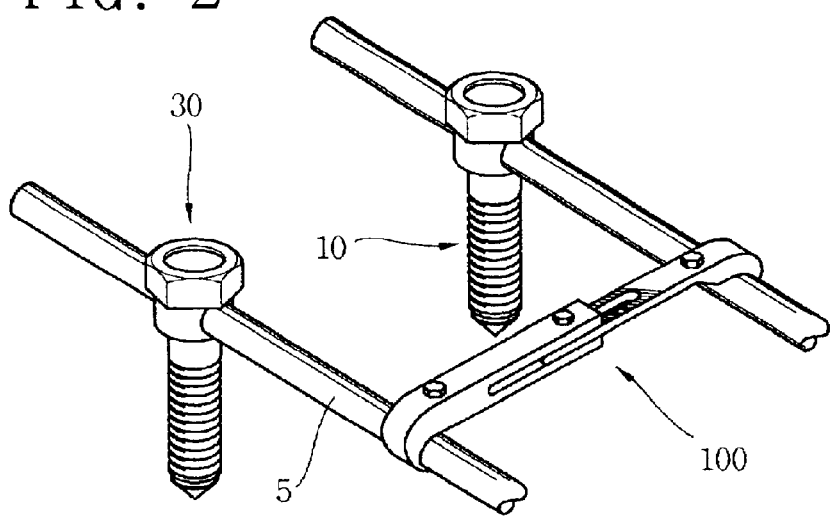
FIG. 2 is a perspective view of the spine-fixing apparatus of FIG. 1.

FIG. 1 and FIG. 2 are respective front elevation view perspective view of the spine-fixing apparatus according to a first preferred embodiment of the present invention.

Generally, when the spine 1 is unstable caused by a fracture or disease, a fixing apparatus is used to stably fix the spine 1.

Referring to FIG. 1 and FIG. 2, spine screw members 10 are coupled to certain portions of each of the spine 1 in a predetermined interval. The spine screw members 10 are continuously arranged in two rows along the spine 1. The spine screw members 10 fixed to the spine 1 are connected by a pair of rods 5, which support the spine 1 in the longitudinal direction through the spine screw members 10. On the spine screw members 10 are separatively installed pressing members 30 to press the rods 5 toward the spine screw members 10.

Figure 3:
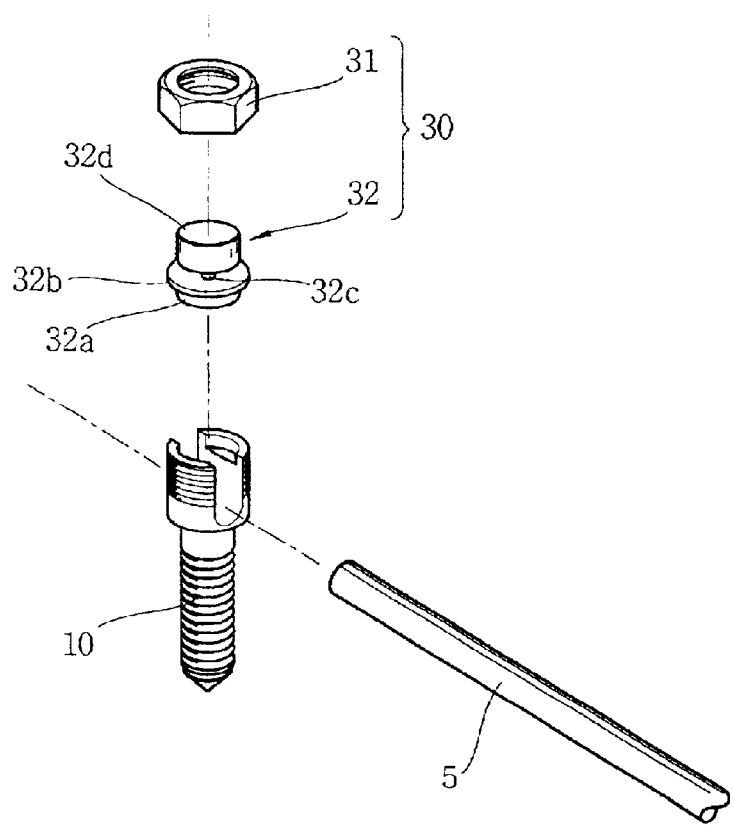
FIG. 3 is an exploded perspective view of a pressing portion of the spine-fixing apparatus of FIG. 1.
Figure 4:
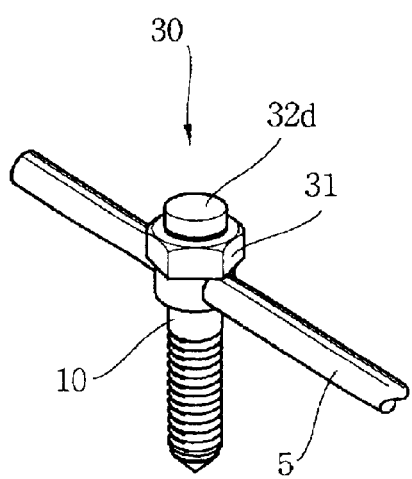
FIG. 4 is an assembled perspective view of the pressing portion of the spine-fixing apparatus according to a first embodiment of the present invention.

As shown in FIG. 3 and FIG. 4, each of the pressing member 30 comprises a pressing piece 32 inserted into an opening formed at the upper end of the spine screw member 10 for pressing the upper surface of the first or second rod and a fixing nut 31 for being coupled with the spine screw member 10 at the upper periphery while surrounding the pressing piece 32.

The pressing piece 32 comprises a pressing protrusion 32a inserted into the opening at the upper end of the spine screw member 10, a catch plate 32b stepped on the top of the pressing protrusion 32a for being caught by the upper end of the spine screw member 10, and a guide protrusion 32d on the top of the catch plate 32b for guiding the fixing nut 31.

The pressing protrusion 32a has a shape of a short cylinder so as to be easily inserted into the opening at the upper end of the spine screw member 10, and an end surface of the cylinder is formed having a grid pattern so as to prevent the rod 5 from sliding to and fro after the fixing nut 31 is screwed down. Also, the guide protrusion 32d has the shape of a cylinder such that the fixing nut 31 can be guided along the guide protrusion 32d in order for the fixing nut 5 to be accurately coupled with the spine screw member 10, and a neck 32c is formed around the guide protrusion at its lower end connected to the catch plate 32b such that the guide protrusion 32d can be removed after fastening the fixing nut 31 to the spine screw member 10.

The rods 5 arranged along the spine 1 are mutually connected by the bridge member 100 in such a way that a distance between the two rods 5 can be by the bridge member 100.

Figure 5:
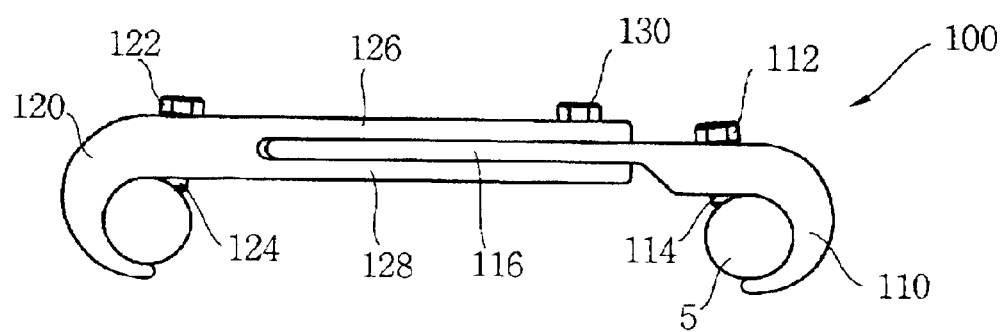
FIG. 5 is a top view of a bridge member of the spine-fixing apparatus of FIG. 1.

FIG. 5 shows the bridge member 100 of the spine fixing apparatus according to the invention.

Referring to FIG. 5, the bridge member 100 is comprises a first and second bridge members 110 and 120. The first bridge member 110 is bent inward at its distal end so as to partially grip the rod 5 and is provided with extended portion at its proximal end toward the other rod 5. It is preferred that the distal end of the bridge member 110 is bent as much as 180° enough so as to prevent the rod 5 from being separated therefrom.

Further, the first bridge member 110 has a screw hole at its distal end portion such that a fixing screw 112 is penetrated and contacted the rod 5 to fix the rod 5. It is preferred that the fixing screw 112 is slightly inclined toward the rod 5, and more preferably, inclined at about 5°. Further, the fixing screw 112 has a curved end 114 corresponding to a round surface of the rod so as to enlarge the friction surface therebetween, resulting in more reliable fixation.

The distal end of the first bridge member 110 is tapered while extending around the rod 5. Here, it is structurally preferable that the end of the first bridge member 110 is roundly finished while surrounding the rod 5 for easy coupling with the rod 5.

Figure 6:
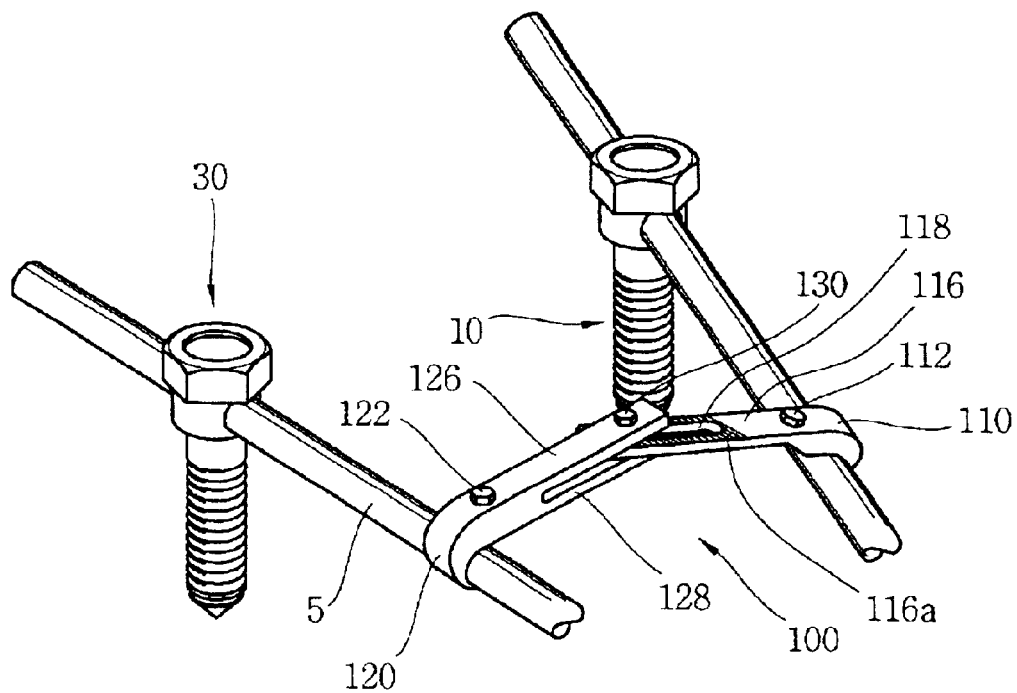
FIG. 6 is a perspective view of the spine-fixing apparatus for illustrating an operation of the bridge member of the spine-fixing apparatus.

The first bridge member 110 has an extension 116 with a slot 118 formed along the longitudinal direction of the extension 116 (see FIG. 6). The slot 118 is long as much as one third of the length of the extension 116 and rounded at both ends thereof. Furthermore, uneven portions 116a are formed on an upper and lower surfaces of the extension 116 around the slot 118. so as to enhance friction force.

The second bridge member 120 is substantially arranged in the opposite direction to the first bridge member 110 and has a screw hole at its distal end such that a fixing screw 122 is penetrated and contacted the other rod 5 to fix the rod. The fixing screw 122 of the second bridge 120 is longer than the first fixing screw 112 corresponding to the thickness of the second bridge member 120. Also, the fixing screw 122 of the second connector 120 preferably has curved end corresponding to a round surface of the rod so as to enlarge the friction surface therebetween, resulting in more reliable fixation.

The second bridge member 120 has a upper and lower extensions 126 and 128 extended toward the rod 5 coupled with the first bridge member 110. The upper and lower extensions 126 and 128 are formed with a predetermined distance therebetween such that the extension 116 of the first bridge member 110 is placed between the upper and lower extensions 126 and 128. It is preferred that the extension 116 of the first bridge member 110 and the upper and lower extensions 126 and 128 of the second bridge member 120 preferably have the same thickness.

The upper and lower extensions 126 and 128 of the second bridge member 120 have holes at the same positions thereof such that an adjustment screw 130 penetrates through the hole of the upper extension 126 of the second bridge member 120, the slot 118 of the extension of the first bridge member 110, and hole of the lower extension 128 of the second bridge member 120 in order. The hole of the lower extension 128 is threaded on its inner wall such that the adjustment screw 130 is screwed into the lower extension 128. Accordingly, when the adjustment screw 130 is screwed down, the upper and lower extensions 126 and 128 of the second bridge member 120 are fixedly coupled with the extension 116 of the first bridge member 110. It is preferred that the hole of the upper extension 126 has the diameter slightly larger than that of the lower extension 128.

Since the slot of the first bridge member 110 is elongated in longitudinal direction of the extension 116, it is possible to adjust the distance between the rods 5 by sliding the adjustment screw 130 along the slot 118 while the adjustment screw is loosed.

Also, the first bridge member and the second bridge member is pivotally connected on the axis of the adjustment screw 130 such that the first and second bridge members can be adjusted according to the shape of the spinebefore being fixed. The upper and lower surfaces of the first bridge member around the slot 118 have the uneven portions 116a so that the first bridge member and the second bridge member can be tightly coupled to each other.

Figure 7:
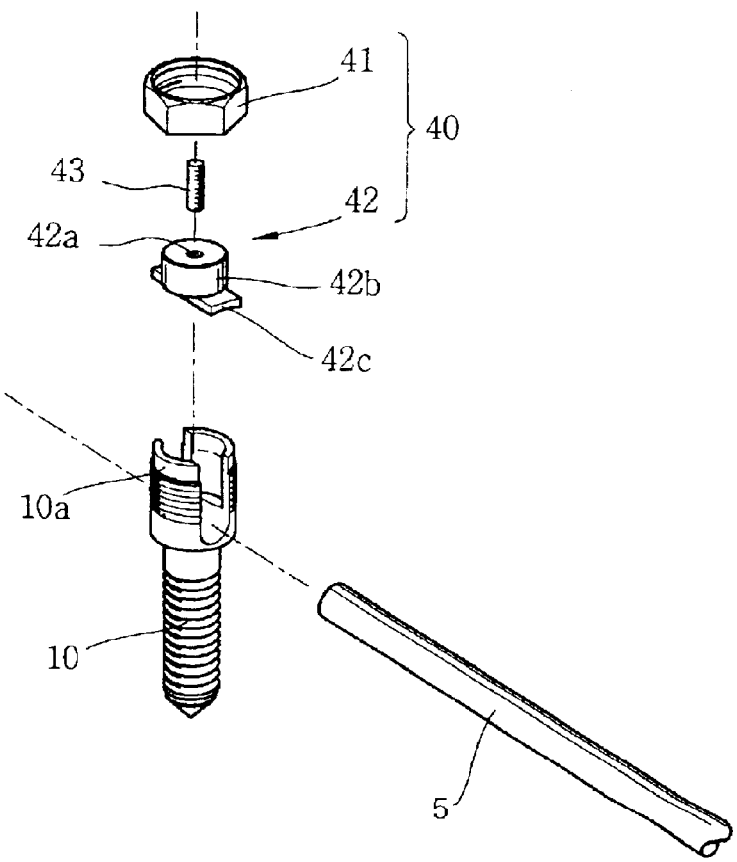
FIG. 7 is an exploded perspective view of a pressing portion of the spine-fixing apparatus according to a second embodiment of the invention.
Figure 8:
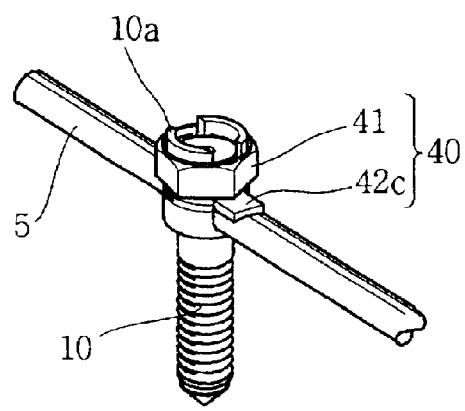
FIG. 8 is an assembled perspective view of the pressing portion of FIG. 7.

FIG. 7 and FIG. 8 are respective the exploded perspective view and assembled perspective view of the spine-fixing apparatus according to a second embodiment of the invention.

As shown in FIG. 7 and FIG. 8, the spine-fixing apparatus according to the second embodiment of the invention comprises spine screw members 10 fixedly coupled to the spine in a predetermined interval, a first and second rods 5 coupled to the spine screw members 10 for supporting the spine, and pressing members 40 for respectively pressing the first and second rods 5 toward the spine screw members.

Each of the pressing members 40 comprises a fixing nut 41 and a pressing piece 42 inserted into an opening formed at a head of each of the spine screw members 10 so as to press the upper surface of each of the first and second rods 5.

Each of the spine screw members 10 has a guide portion 10a upwardly extended for guiding the fixing nut 41. The fixing nut 41 has an inner diameter slightly greater than that of the guide portion 10a so that the guide portion 10a of the spine screw member 10 can be inserted into the fixing nut 41.

The pressing piece 42 is provided with a pressing plate 42c for pressing the upper surface of the rod 5, and a cylindrical supporting portion 42b formed on an upper surface of the pressing plate 42c for being guided along the inner surface of the spine screw member 10.

Also, the pressing plate 42c and the supporting portion 42b of the pressing piece 42 is provided with a through hole 42a formed at the center thereof such that an internal fixing screw 43 is screwed therein for fixing the rods 5.

The guide portion 10a of the each spine screw member 10 allows the fixing nut 41 to be guided onto the upper end of the spine screw member 10. After the fixing nut 41 is fastened, the guide portion 10a can be removed from the spine screw member 10 after the installation of the spine-fixing apparatus because a grooved neck is formed between the guide portion 10a and the spine screw member 10. Further, the rod 5 can be further pressed by the internal fixing screw 43 being inserted into a central hole of the pressing piece 42.

Figure 9:
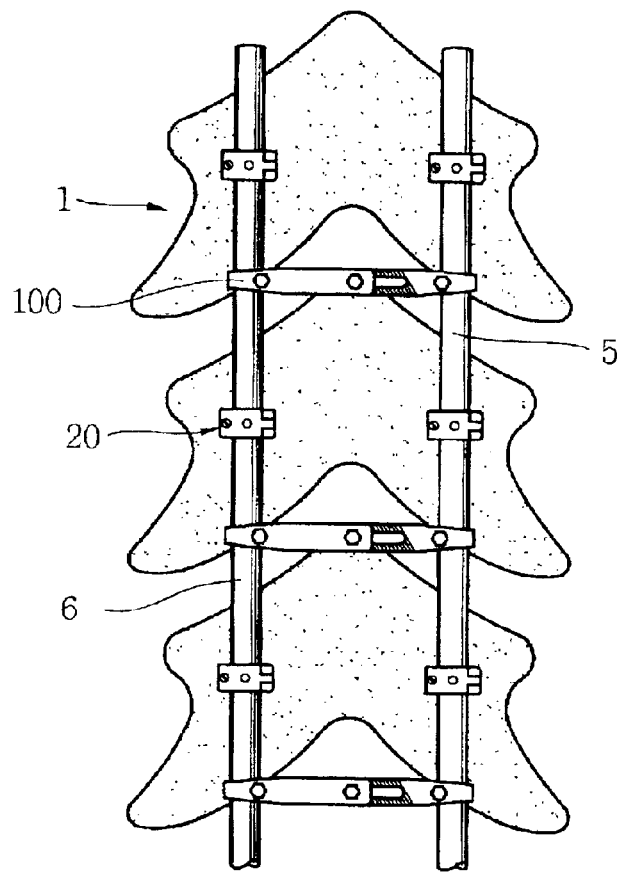
FIG. 9 is a front elevation view of a spine-fixing apparatus installed on spine according to a third embodiment of the invention.
Figure 10:
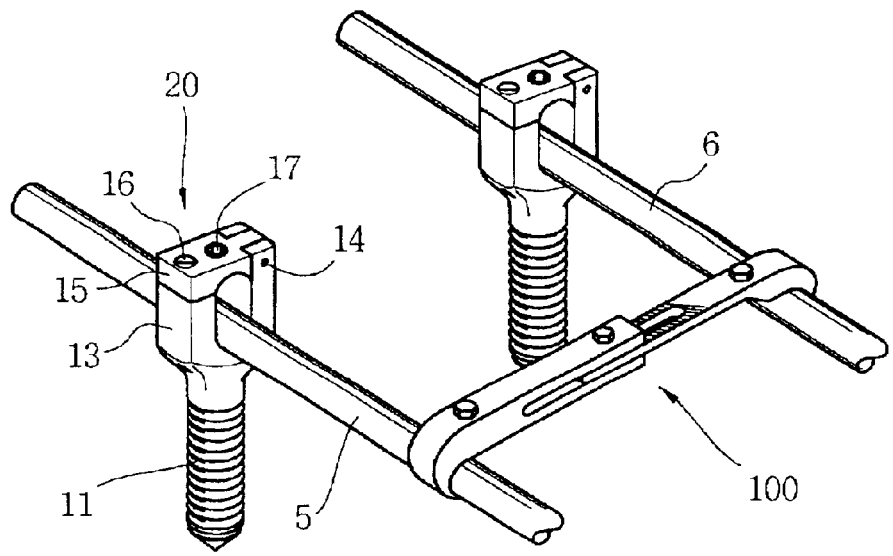
FIG. 10 is a perspective view of the spine-fixing apparatus of FIG. 9.
Figure 11:
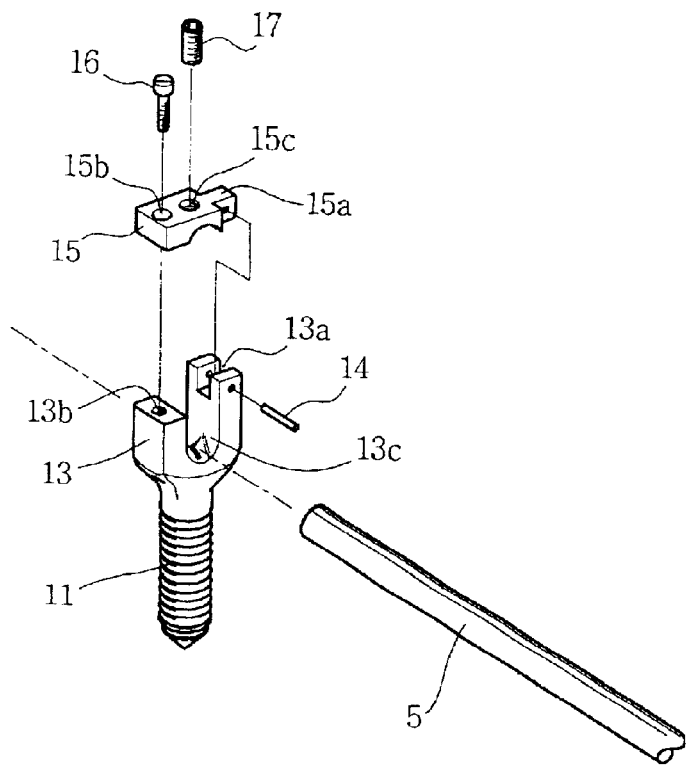
FIG. 11 is an exploded perspective view of a spine screw member of the spine-fixing apparatus of FIG. 9.
Figure 12:
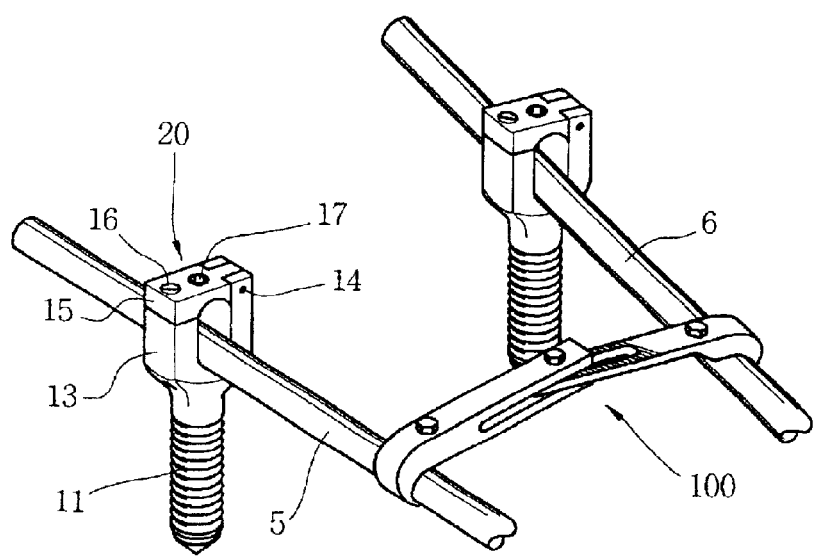
FIG. 12 is a perspective view of the spine-fixing apparatus for illustrating an operation of the bridge member of the spine-fixing apparatus according to the third embodiment of the present invention.

FIG. 9 and FIG. 10 are respective front elevation and perspective views of the spine-fixing apparatus according to a third embodiment of the invention, FIG. 11 is an exploded perspective view of a spine screw member of the spine-fixing apparatus according to the third embodiment of the invention, and FIG. 12 is a perspective view of the of the spine fixing apparatus for illustrating an operation of the bridge member of the spine-fixing apparatus according to the third embodiment of the invention.

Referring to FIG. 9 to FIG. 12, each of spine screw members 20 comprises a screw portion 11 to be inserted into the spine 1 in a predetermined depth, a supporting portion 13 formed on top of the screw portion 11 for receiving and supporting rod 5(6), and a cover 15 pivotally mounted on top of the supporting portion 13 for fixing the rod 5(6) received in a groove which divides the supporting portion 13 into two branches.

The supporting portion 13 has a recess 13a at upper end of one branch thereof and the cover 15 has a coupling protrusion 15a at one end corresponding to the recess 13a such that the coupling protrusion 15a of the 15 and the recess 13a of the supporting portion 13 are engaged each other and pivotally connected by means of a hinge pin 14. Also, in order to fasten the other side of the cover 15 to the supporting portion 13, the supporting portion 13 has a fastening hole 13b at upper end of other branch thereof, the cover 15 has a threaded hole 15b formed at an opposite end portion of the coupling protrusion 15a corresponding to the threaded hole 15b such that the cover 15 is fixed to the supporting portion 13 by a fastening screw 16 being screwed into the threaded hole 15b and the fastening hole 13b.

The cover 15 has another threaded hole 15c formed at a center thereof in parallel with the thread hole 15b such that another internal fixing screw 17 is screwed down into the threaded hole 15c in order to fixedly press the upper surface of the rod 5(6).

The operation of the above structured spine-fixing apparatus will be described hereinafter.

Firstly, the screw portions 11 of the spine screw members 20 are fixedly screwed into the spine 1 to be supported. The first and second rods 5 and 6 are received in the U-shaped grooves 13c formed on the supporting portions 13 such that the rods 5 and 6 are settled on the bottom of the U-shaped grooves 13c.

After the first and second rods 5 and 6 are arranged in the grooves 13c, the covers 15 on the top of the spine screw members are pivoted so as to cover the upper ends of the spine screw members 20.

Next, the fastening screw 16 is screwed down through the threaded hole 15b of the cover and the screw hole 13b of the supporting portion 13 so as to fix the cover 15 to the supporting portion 13. After the cover 15 is fixed to the supporting portion 13, the internal fixing screw 17 is screwed down through the screw hole 15c of the cover of the spine screw member 20 so as to fixing the rod 5(6) by the lower end of the internal fixing screw pressing the upper surface of the fixing rod(6).

After the spine screw members 20 are completely assembled like this, as shown in FIG. 12, the distance and angle between the first and second rods 5 and 6 are adjusted using a bridge 100 so that the spine 1 can be reliably supported in the optimum conditions.

The present invention described hereinbefore is not limited to the foregoing description of the embodiments, whereas various variations and modifications can be made by those skilled in the art without departing from the spirit and scope of the invention defined by the appended claims.

As described above, in the spine-fixing apparatus of the present invention the distance and angle between the rods can be adjusted such that the spine-fixing apparatus can be installed in optimal formation according to the shape of the spine.

Also, since the spine-fixing apparatus of the present invention is provided with a guide member at the upper end of the spine screw member, the fixing nut can be guided such that the spine-fixing apparatus provide reliable fixation of the spine.

Furthermore, the screw portion of the screw member, supporting member for supporting the rod, and the cover for fixing the rod to the supporting member of the spine-fixing apparatus are integrally formed, the installation process of the spine-fixing apparatus is simplified, resulting in reducing overall installation time.

What is claimed is:

1. A spine fixing apparatus comprising:
   a plurality of spine screw members fixedly coupleable to a spine in a predetermined interval;
   a pair of rods coupled to the spine screw members for supporting the spine;
   a plurality of fixing nuts coupled to the spine screw members;
   a plurality of pressing pieces interposed between the fixing nuts and the spine screw members for pressing and fixing rods; and
   a plurality of unthreaded guiding portions extending from upper ends of threaded portions of the spine screw members in the longitudinal direction of the spine screw members for respectively guiding the fixing nuts,
   wherein each of the pressing members is provided with a coupling hole formed at the center of the pressing member coaxial with the spine screw member and an inner fixing screw inserted in to the coupling hole for fixedly pressing the upper surface of the rod.

2. The spine fixing apparatus according to claim 1, wherein a neck is provided between each guiding portion and each of the spine screw members, such that the guiding portion can be removed after the fixing nut is fastened.

3. A spine fixing apparatus comprising:
   a plurality of spine screw members fixable to a spine in a predetermined interval;
   first and second role coupled to the spine screw members for supporting the spine; and
   a bridge having a first bridge member for being coupled to the first rod, and second bridge member for being coupled to the second rod, and an adjustment screw for coupling the first bridge member to the second bridge member while adjusting distance and angle between the first and second rods,
   wherein the adjustment screw is inserted into a through hole formed on an upper extension of the second bridge member, a slot formed on an extension of the first bridge member, and a through hole formed on a lower extension of the second bridge member such that the adjustment screw freely slides along the slot of the first bridge member to adjust the distance and angle between the first and second rods.

4. The spine fixing apparatus according to claim 3, wherein the first bridge member has a bumpy friction surface around the slot so as to enhance friction force when the adjustment screw is fastened.

* * * * *